(12) United States Patent
Hashimoto et al.

(10) Patent No.: US 7,090,984 B2
(45) Date of Patent: Aug. 15, 2006

(54) DEVICE AND METHOD FOR DETECTING SUBSTANCE

(75) Inventors: Koichi Hashimoto, Zama (JP);
Yoshitsugu Harada, Zama (JP);
Shigetoshi Okubo, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 327 days.

(21) Appl. No.: 10/182,477

(22) PCT Filed: Oct. 25, 2001

(86) PCT No.: PCT/JP01/09396

§ 371 (c)(1),
(2), (4) Date: Jul. 29, 2002

(87) PCT Pub. No.: WO02/37108

PCT Pub. Date: May 10, 2002

(65) Prior Publication Data

US 2003/0040106 A1    Feb. 27, 2003

(30) Foreign Application Priority Data

Oct. 27, 2000  (JP)  ............................. 2000-328941
Jun. 27, 2001  (JP)  ............................. 2001-195134

(51) Int. Cl.
*G01N 33/53*   (2006.01)

(52) U.S. Cl. .................. 435/7.1; 435/7.5; 435/7.92; 435/7.93; 435/7.94; 435/287.1; 435/287.2; 435/287.7; 435/287.9; 435/805; 436/514; 436/518; 436/510; 436/512; 436/513; 436/524; 436/525; 436/528; 436/531; 436/169; 436/174; 436/810; 422/56; 422/58

(58) Field of Classification Search ................ 436/514, 436/518, 510, 512, 513, 524, 525, 528, 531, 436/169, 174, 805, 810; 435/7.1, 7.5, 7.92, 435/7.93, 7.94, 287.1, 287.2, 287.7, 287.9, 435/805; 422/56–68
See application file for complete search history.

(56) References Cited

U.S. PATENT DOCUMENTS

| | | | | | |
|---|---|---|---|---|---|
| 4,219,335 | A | * | 8/1980 | Ebersole | 436/518 |
| 5,622,871 | A | * | 4/1997 | May et al. | 436/514 |
| 5,821,073 | A | * | 10/1998 | Lee | 435/7.92 |
| 5,945,345 | A | * | 8/1999 | Blatt et al. | 436/518 |
| 6,087,184 | A | * | 7/2000 | Magginetti et al. | 436/514 |
| 6,248,598 | B1 | * | 6/2001 | Bogema | 436/518 |

FOREIGN PATENT DOCUMENTS

| | | |
|---|---|---|
| JP | 05-052836 | 3/1993 |
| JP | 06-289024 | 10/1994 |
| JP | 10-096728 | 4/1998 |

OTHER PUBLICATIONS

*The Medical and Test Journal*, No. 706, p. 5, Oct. 11, 1999.

* cited by examiner

*Primary Examiner*—Bao-Thuy L. Nguyen
(74) *Attorney, Agent, or Firm*—Knobbe, Martens, Olson & Bear, LLP

(57) ABSTRACT

A method for detecting a substance, comprising developing a developing liquid through a test region up to a reference region, and a detection device for use therein, wherein the reference region comprises a metal compound other than an alkali metal salt, and the developing liquid that reaches the reference region contains a label that can be accumulated in the reference region. The label is preferably a colored particle, and is preferably bound to an antibody or an antigen.

14 Claims, 5 Drawing Sheets ical field

DEVICE AND METHOD FOR DETECTING SUBSTANCE

This is the U.S. National Phase under 35 U.S.C. § 371 of International Application PCT/JP 01/09396, filed Oct. 25, 2001, which claims priority of Japanese Patent Application No. 2000-328941, filed Oct. 27, 2000 and Japanese Patent Application No. 2001-195134 filed Jun. 27, 2001.

TECHNICAL FIELD

The present invention relates to detection of a substance using a solution development method. In particular, the present invention relates to a device (test piece) and a method for detecting a substance, in which completion of development can be confirmed or semi-quantitative measurement can be made.

BACKGROUND ART

As means for diagnosing diseases, generally used are methods for detecting a causative substance (for example, antigen) existing in a test sample, for example, fluid such as serum and urine, culture broth, extract, feces or the like or its related substance (for example, antibody). Conventionally, amount of a test substance such as an antibody or antigen in a test sample is measured by utilizing a biologically specific reaction such as an antigen-antibody reaction. As a kind of such detecting methods, the solution development method (chromatographic method) including an immunochromatographic method has been proposed heretofore (The Medical & Test Journal, No. 706, p.5, Oct. 11, 1999).

The solution development method is a technique in which a sample is applied to a part of a test piece and penetrated and developed in the test piece material usually by using a developing liquid such as water to detect a test substance existing in the sample. In the immunochromatographic method, which is one type of the solution development method, an immune complex formed between a test substance and a substance corresponding to the test substance is detected in a test region by using a labeled reagent.

In the solution development method, in order to confirm whether a developing liquid containing a test substance penetrates into a test region of the test piece and the development is completed, that is, completion of the test, the test piece can be provided with a specific site called a development completion confirming region. A development completion signal is a requirement to be satisfied by the test system upon determination of a test result, that is, it plays a role of presenting the fact that "a specific amount of developing liquid has passed through a test region together with a labeled reagent over a certain time, and has further reached the development completion confirming region", and is a test completion signal for a practitioner of the test. Confirmation of the signal is important to make the test result reliable. For example, it is important for determining that the test result is negative (no reaction is observed) or the like.

As a method for confirming a development completion signal, there are known a method of adding a substance that undergoes an antigen-antibody reaction into the development completion confirming region, a method of adding an indicator that develops color or changes in its color in response to a change in pH into the development completion confirming region and so forth.

Further, the solution development method has been utilized as a qualitative determination method because of its detection accuracy.

DISCLOSURE OF THE INVENTION

However, in conventional techniques concerning the aforementioned confirmation of completion of development, a biological material should be used as an antigen or antibody when a specific reaction based on an antigen-antibody reaction is utilized. Therefore, problems arises that much labor is required for preparation and that manufacturing cost becomes high. Furthermore, there is also a problem that it is difficult to obtain constant activity among preparation lots.

Further, when an indicator that develops color or changes in its color in response to change in pH is used, there is a problem that discoloration is likely to occur when the test piece is dried during storage, thereby resulting in poor data storability.

An object of the present invention is to provide a novel device and method for detecting a substance using a novel method for confirming a development completion signal, which is free from the aforementioned problems, that is, which is readily prepared and manufactured at a low cost, shows no fluctuation among preparation lots and is hardly discolored to provide favorable data storability.

Another object of the present invention is to provide a device and method that enable semi-quantitative measurement based on the solution development method.

In view of the aforementioned conventional techniques, the inventors of the present invention tested various methods for generating signals in order to provide a method for confirming a development completion signal free from the aforementioned problems.

As a result, the inventors of the present invention found that, if a metal compound other than an alkali metal salt was applied to a nitrocellulose membrane, a development carrier commonly used in the immunochromatographic method, the metal compound was immobilized relatively firmly. That is, it was found that the metal compound applied to the nitrocellulose membrane was maintained at an applied position without flowing out even when at least a buffer (aqueous solution) commonly used in the immunochromatographic method is developed in the membrane.

Furthermore, as a result of many examinations, the inventors of the present invention found that, if a metal compound other than an alkali metal salt was applied to a specific position on a nitrocellulose membrane, it did not affect flow of a developing liquid itself at all, but it had an effect of blocking flow of particles floating in the developing liquid. That is, it was found that, if a protein labeled with colored particles such as gold colloid and latex (labeled substance) or the like was developed with a developing liquid, the flow of the labeled substance was blocked in a region to which metal compound was applied, and as a result of accumulation of the labeled substance, existence of the labeled substance that was invisible in a diffusion state became visible and hence a development completion signal could be confirmed.

Based on the aforementioned findings, the inventors of the present invention assiduously studied aiming at its practical use. As a result, it was found that, in detection of a substance using the solution development method, if a metal compound other than an alkali metal salt was contained in a reference region for confirming develop completion and a label that could accumulate in the reference region was contained in a developing liquid reaching the reference region, there could be provided a device for detecting a substance which could overcome the aforementioned problems, be readily prepared and manufactured at a low cost, showed no fluctuation among preparation lots and be hardly discolored to provide favorable data storability and a detecting method utilizing it.

Furthermore, they found that, if a metal compound other than an alkali metal salt was contained in the reference region to generate a signal, the signal could be controlled to have desired intensity by controlling the content of the metal compound.

The present invention was accomplished based on these findings.

In a first aspect of the present invention, it is provided a device for detecting a substance used for a solution development method in which a developing liquid is developed through a test region up to a reference region, wherein the reference region comprises a metal compound other than an alkali metal salt, and the developing liquid that reaches the reference region contains a label that can be accumulated in the reference region (hereafter, also referred to as "detection device of the present invention").

In the detection device of the present invention, the label is preferably a colored particle. Further, the label is preferably bonded to an antibody or an antigen. Further, a development carrier of the detection device is preferably a nitrocellulose membrane.

Further, in the detection device of the present invention, the reference region preferably comprises the metal compound other than the alkali metal salt so that a signal having intensity equivalent to intensity of a signal generated in the test region when the developing liquid containing a predetermined amount of a substance to be detected is developed should be generated in the reference region. In this case, it is further preferred that the detection device of the present invention comprises a plurality of development carriers each having a test region and a reference region, and intensity of a signal generated in each reference region should be equivalent to intensity of a signal generated in each corresponding test region when developing liquids containing a substance to be detected in different predetermined amounts are developed.

In a second aspect of the present invention, it is provided a method for detecting a substance, comprising developing a developing liquid through a test region up to a reference region, wherein the reference region comprises a metal compound other than an alkali metal salt, and the developing liquid that reaches the reference region contains a label that can be accumulated in the reference region (hereafter, also referred to as "the detection method of the present invention").

In the detection method of the present invention, the label is preferably a colored particle. Further, the label is preferably bonded to an antibody or an antigen. Furthermore, the development carrier of the detection device is preferably a nitrocellulose membrane.

Further, in the detection method of the present invention, it is preferred that the reference region should comprises the metal compound other than the alkali metal salt so that a signal having intensity equivalent to intensity of a signal generated in the test region when the developing liquid containing a predetermined amount of a substance to be detected is developed should be generated in the reference region, and the method preferably comprises comparing the intensity of the signal generated in the test region with the intensity of the signal generated in the reference region. In this case, it is more preferred that a plurality of development carriers each having a test region and a reference region are prepared, and intensity of a signal generated in each reference region is equivalent to the intensity of a signal generated in each corresponding test region when developing liquids containing the substance to be detected in different predetermined amounts are developed.

BEST MODE FOR CARRYING OUT THE INVENTION

Figure 1:
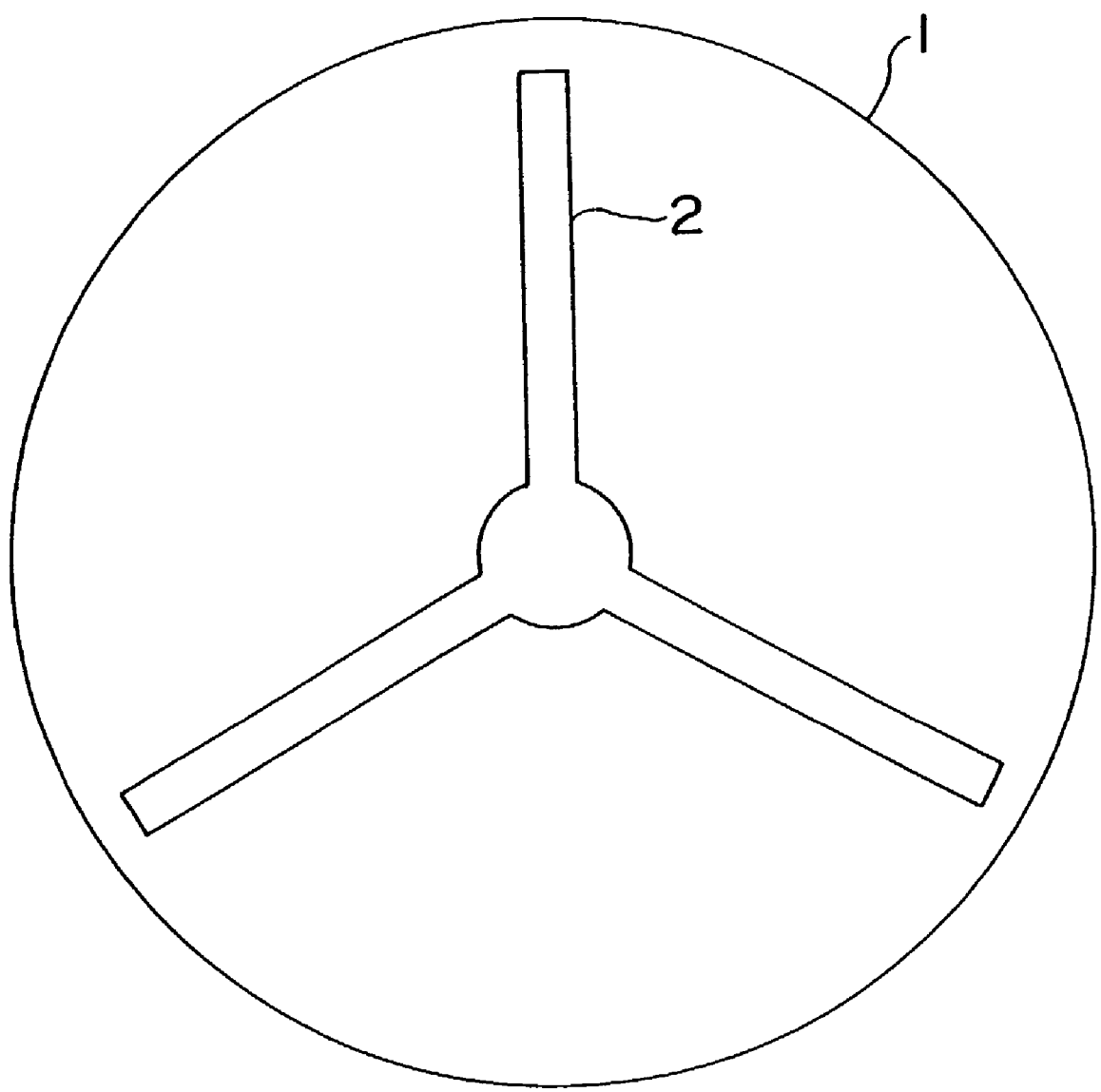
FIG. 1 shows an exemplary substrate constituting the detection device of the present invention comprising a plurality of strips.

Hereafter, the present invention will be specifically explained. In the present specification, percentage is represented in terms of weight unless otherwise specified.

The detection device of the present invention is a device for detecting a substance used in a solution development method in which a developing liquid is developed through a test region up to a reference region, wherein the reference region comprises a metal compound other than an alkali metal salt, and the developing liquid that reaches the reference region contains a label that can be accumulated in the reference region.

The detection device of the present invention is a kind of device for detecting a substance used for a solution development method. The detection device of the present invention may have the same configuration as a conventional detection device except that a metal compound that is not an alkali metal salt is contained in the reference region and a label that can be accumulated in the reference region is contained in the developing liquid that reaches the reference region. That is, the detection device of the present invention can be used in various embodiments of substance-detecting device used for a solution development method. Specifically, a conjugate pad (for example, those produced by Millipore etc.) that receives a specimen can be bonded to the lower end (upstream region) of the detection device (test piece), the detection device (test piece) can be supported with a support composed of a synthetic resin or the like, an absorbing pad for absorbing a developing liquid can be bonded to the upper end (downstream region) of the detection device (test piece), and so forth.

The solution development method is a method also called chromatography. In the solution development method, a test region is provided on a development carrier, and a developing liquid containing a substance to be detected is developed through the development carrier. In the test region, a reaction occurs between the substance to be detected and a substance reactive with the substance to be detected, and the substance to be detected can be detected by detecting this reaction. The reaction is typically detected by using Reactive substance 1 immobilized on the test region and labeled Reactive substance 2, and detection is performed by developing a developing liquid containing the substance to be detected and Reactive substance 2 in the development carrier through the same phenomenon as in paper chromatography to allow formation of a complex of Reactive substance 1 and Reactive substance 2 sandwiching the substance to be detected when a developing liquid flow reaches a site where Reactive substance 1 is immobilized (test region) on the development carrier and detecting the label occurring in the test region at that time.

The reactive substance means a substance that reacts with a substance to be detected based on a biologically specific reaction such as a reaction of an antibody and an antigen, a reaction of a sugar chain and lectin and a reaction of a ligand and a receptor.

The developing liquid is water, buffer or the like and may be any of these dissolving a specimen containing a substance to be detected. When the specimen containing a substance to be detected is a liquid, the specimen itself or a specimen solution diluted with water, buffer or the like can also be the developing liquid.

As the most typical chromatography method in the field of clinical examination, immunochromatography can be exemplified, in which the labeled reactive substance is an antibody or an antigen. The immunochromatography is typically a method using Antibody 1 immobilized on a development carrier and Antibody 2 labeled with colored particles. A developing liquid containing a substance to be detected and Antibody 2 are developed on the development carrier, and when the developing liquid flow reaches a site where Antibody 1 is immobilized (test region) on the development carrier, there is formed a complex comprising Antibody 1 and Antibody 2 sandwiching the substance to be detected. At this time, color tone of the colored particles is observed on the membrane, and existence of the substance to be detected can be visually confirmed.

The reference region is a region for confirming completion of development and/or generating a signal serving as a reference when the signal of the test region is evaluated, that is, a reference signal.

Since the metal compound contained in the reference region existing downstream from the test region does not affect an antigen-antibody reaction or the like in the test region at all, the reference region preferably exists in a region downstream from the test region in the developing direction. Furthermore, when the reference region in the detection device of the present invention is a region for confirming completion of the development, it needs to exist in a region downstream from the test region on the development carrier in the developing direction.

Examples of the metal compound that is not an alkali metal salt used in the detection device of the present invention include various metal compounds such as calcium acetate monohydrate, lanthanum acetate n-hydrate, lanthanum chloride heptahydrate, cerium acetate monohydrate, cerium(III) chloride heptahydrate, praseodymium acetate n-hydrate, neodymium acetate n-hydrate, erbium acetate tetrahydrate, manganese acetate tetrahydrate, iron(II) sulfate heptahydrate, ammonium iron(II) sulfate hexahydrate, cobalt(II) acetate tetrahydrate, nickel(II) acetate tetrahydrate, copper(II) acetate monohydrate, copper(II) chloride dihydrate, copper(II) sulfate pentahydrate, zinc(II) acetate dihydrate, cadmium(II) acetate dihydrate, aluminum acetate (water-soluble), aluminum potassium sulfate dodecahydrate and lead(II) acetate trihydrate, and commercially available products of these can be used. As is evident from the test examples described later, alkali metal salts are excluded because alkali metal salts such as sodium bromide and potassium chloride are hard to be immobilized on a development carrier, and since they flow out with a developing liquid even when they are applied, a flow of label of colored particles and so forth cannot be blocked. Further, it is preferable to avoid use of a metal compound originally having intense color such as potassium permanganate and a metal compound easily developing color when brought into contact with moisture in air such as anhydrous copper sulfate and anhydrous cobalt chloride, since such metal compounds may invite erroneous recognition, inhibition or the like of the development completion signal. Therefore, it is preferable to exclude potassium permanganate, anhydrous copper sulfate and anhydrous cobalt chloride from the metal compounds used for the present invention. Furthermore, as shown in the test examples described later, when gold colloid having a relatively small particle size of 15 nm as colored particles, metal compounds comprising lanthanide elements, of which representative examples are lanthanum acetate n-hydrate, lanthanum chloride heptahydrate, cerium acetate monohydrate, cerium(III) chloride heptahydrate, praseodymium acetate n-hydrate, neodymium acetate n-hydrate and erbium acetate tetrahydrate, and metal compounds comprising iron, of which representative examples are iron (II) sulfate heptahydrate and iron(II) ammonium sulfate hexahydrate, are particularly preferred because of their excellent coloring property.

As the development carrier, a membrane of a porous substance that can be used for chromatography can be used so long as the metal compound applied thereon is maintained at the applied position even when a developing liquid is developed through the membrane. As such a membrane, a nitrocellulose membrane is preferred, and a nitrocellulose membrane having a pore size of 3–12 μm, which is commonly used in immunochromatography that constitutes a preferred embodiment of the present invention, can be exemplified.

The method for allowing the aforementioned metal compound to be contained in the reference region may be a method of applying an aqueous solution of the metal compound to the reference region of the development carrier. Hereafter, a detection device for immunochromatography using a nitrocellulose membrane as a development carrier will be explained as an example.

In immunochromatography, in general, a required protein is applied to a nitrocellulose membrane, and then so-called blocking and subsequent washing are performed. The metal compound is applied after these operations. The metal compound is usually applied as an aqueous solution of a water-soluble salt thereof, and in this case it may be applied with addition of a small amount of alcohols in order to lower surface tension of the solution and reduce electrostatic repulsion. The washing operation is usually performed in many cases by using a weak basic buffer of about pH 7.5 containing a moistening agent such as sodium dodecylsulfate. This does not particularly need to be changed for the present invention, and it is rather preferable to perform washing with a weak basic buffer before application. After the application, the applied membrane is dried overnight at 35° C. and stored at room temperature and humidity of 30–50%.

Usually, the amount of the metal compound applied on the nitrocellulose membrane is preferably 0.2–400 μg/cm$^2$, more preferably 1.0–40 μg/cm$^2$.

In the detection device of the present invention, intensity of a signal to be generated in the reference region can be changed by controlling the amount of the solution to be applied through control of concentration of the metal compound, discharge amount of the solution to be applied, sweeping speed of an applicator and so forth upon application. For example, the amount of the solution to be applied can be adjusted so that a signal having intensity equivalent to intensity of a signal generated in the test region when a developing liquid containing a predetermined amount of a substance to be detected is developed should be generated in the reference region.

It is known that many of metal elements except for alkali metals form a hardly water-soluble hydroxide or a basic salt a part of which is replaced with a hydroxyl group and are precipitated under a basic condition in an aqueous solution. Further, there are also known metal elements that absorb carbon dioxide in air and change into a hardly water-soluble different chemical species. Therefore, a final chemical species carried on the development carrier is not necessarily the applied one as it is, but is rather likely to change into a salt insoluble in water. This naturally depends on the applied metal compound, and a final chemical species is not necessarily evident even when the metal compound is specified. However, since the effect of the present invention can be obtained by applying the aforementioned metal compounds, it is considered to be appropriate to define the chemical species by the metal compound to be applied.

The label used for a detection device of the present invention is not particularly limited so long as it is a label that can be accumulated in the reference region containing the metal compound. Whether the label can be accumulated in the reference region or not can be determined as described in Test Examples 1 and 2 described later.

A preferred label is a colored particle. As the colored particle, gold colloid, latex and so forth can be exemplified, and those having a relatively large particle size are preferred. The particle size is usually 3–500 nm, preferably 10–300 nm, in terms of a size determined by electron microscopy. The gold colloid having a particle size of at least 15 nm is preferred because of its excellent coloration degree.

The generation of a development completion signal or a reference signal in the reference region of the detection device of the present invention is based on a principle that the label in the developing liquid is blocked and its flow is blocked by making the development carrier contain a metal compound by coating or the like and thereby the labeled is accumulated to generate a detectable (preferably visible) signal. Therefore, it is sufficient if degree of the accumulation is enough to generate a detectable development completion signal or reference signal. Further, it is sufficient if the label is contained in a developing liquid that reaches the reference region, and does not need to be contained in the initial developing liquid applied to the detection device of the present invention. Furthermore, the label may be a label in a labeled reactive substance that has passed through the test region without being captured, or may be a label other than that. In the latter case, for example, a label different from the label used as a label of the reactive substance may be contained in the initial developing liquid, or a label may be contained in a development carrier between the test region and the reference region so as to be movable by the developing liquid.

In the detection device of the present invention, a metal compound that is not an alkali metal salt is preferably contained in the reference region so that a signal of intensity equivalent to intensity of a signal generated in the test region when a developing liquid containing a predetermined amount of a substance to be detected is developed should be generated in the reference region. In this case, it is further preferred that the detection device of the present invention should be provided with a plurality of development carriers each having a test region and a reference region, and intensity of a signal generated in each reference region is equivalent to intensity of a signal generated in each corresponding test region when developing liquids containing the substance to be detected in different predetermined amounts are developed.

As for a signal generated in a test region of device used in the solution development method, it is generally difficult to visually determine signal intensity for a sole signal. However, if another signal is generated for comparison, it is relatively easy to compare intensities of the two signals and thereby determine degree of the intensities. According to the present invention, the signal intensity in the test region can be semi-quantitatively determined based on the fact that a signal generated in the reference region can be adjusted to a desired intensity as described above. That is, when a signal having intensity equivalent to intensity of a signal generated in the test region when a developing liquid containing a predetermined amount of a substance to be detected is developed is generated in the reference region of the detection device of the present invention, semi-quantitative measurement can be performed by comparing intensities of the signals generated in the test region and the reference region.

Hereafter, the above will be explained with reference to specific examples. A certain amount of antibodies that recognize a substance to be detected are applied to the test region of the detection device. When a specimen containing the substance to be detected together with another antibodies labeled with particles is developed through the detection device, the substance to be detected is captured and generates a signal in the test region. The signal intensity at this time varies depending on the concentration of the substance to be detected in the developing liquid, and it is generally difficult to visually determine the concentration of the substance to be detected from its intensity. Therefore, the amount of the metal compound applied to the reference region is adjusted so that intensity of the signal generated in the reference region (hereafter, reference signal) should be equivalent to intensity of a signal generated in the test region (hereafter, test signal) when the concentration of the substance to be detected in the developing liquid is, for example, 500 ng/ml. As a result, if a specimen which has such a concentration of the substance to be detected that its concentration in the developing liquid should become exactly 500 ng/ml is developed through this detection device, visual intensities of the signals generated in the test region and the reference region become the same. However, when the concentration of the substance to be detected in the developing liquid is lower than 500 ng/ml, the test signal becomes weaker than the aforementioned signal, and the reference signal becomes stronger on the contrary. On the other hand, when the concentration of the substance to be detected in the developing liquid exceeds 500 ng/ml, the test signal becomes stronger than the aforementioned signal and the reference signal becomes weaker on the contrary. Thus, by comparing intensities of the test signal and the reference signal on a strip, whether the concentration of the substance to be detected in the developing liquid is about 500 ng/ml, exceeds 500 ng/ml or is lower than 500 ng/ml can be visually determined.

In order to improve determination accuracy, it is preferable to increase the number of development carriers (strips) each having a test region and a reference region. That is, in the above example, the amounts of the antibodies to be applied to the test regions are made constant, and those providing reference signals having intensities corresponding to, for example, 200 ng/ml and 1500 ng/ml, are prepared, in addition to the one showing intensity equivalent to that of a test signal corresponding to 500 ng/ml. That is, three kinds of strips are prepared in which the amount of the antibodies applied to the test region is constant, but a metal compound is applied to the reference regions in different amounts. Namely, these are three kinds of strips consisting of those in which the visual intensity of the reference signal and the visual intensity of the test signal become exactly the same when a specimen solution containing a substance to be detected at a concentration of 200 ng/ml is developed, when a specimen solution containing a substance to be detected at a concentration of 500 ng/ml is developed, and when a specimen solution containing a substance to be detected at a concentration of 1500 ng/ml is developed. Hereafter, these are referred to as Strip A, Strip B and Strip C, respectively. Further, a specimen containing a substance to be detected at an unknown concentration is developed through these three kinds of strips at the same time.

When intensities of color developing signals in the test region and the reference region in Strip A are compared, and if the test signal is weaker than the reference signal, it can be determined that the concentration of the substance to be detected in the specimen is lower than about 200 ng/ml. If the test signal is stronger than the reference signal, intensities of the test signal and the reference signal in Strip B are compared. If the test signal is weaker than the reference signal, it can be determined that the concentration of the substance to be detected in the specimen is higher than about 200 ng/ml but lower than about 500 ng/ml. Thereafter, by the same procedure, the concentration of the substance to be detected in this specimen can be determined in a semi-quantitative manner and classified into grades such as lower than about 200 ng/ml, about 200 ng/ml, between about 200 ng/ml and about 500 ng/ml, about 500 ng/ml, between about 500 ng/ml and about 1500 ng/ml, about 1500 ng/ml and exceeding 1500 ng/ml.

A signal generated in the reference region according to the present invention is preferably equivalent to that of the test region in quality, since such signals can be easily compared by visual inspection. For example, when a signal is generated by a labeled reactive substance passed through the test region without being captured, it is generated by accumulation of the same particle labeled substance as in the case of the signal generated in the test region, and hence these signals become equivalent in quality.

This method for semi-quantifying a substance to be detected based on comparison of intensities of a signal in the test region and a signal in the reference region can also be implemented in principle by an immunochemical reaction, in which a signal is generated by applying anti-antibodies to the reference region to capture labeled antibodies passed through the test region without being captured. However, in this case, in addition to a problem of high manufacturing cost, there are generally difficulties in obtaining constant activity among preparation lots and hence in reproducibility of intensity of a generated signal because biological materials are used. Further, control of appropriate application of anti-antibodies for generating a signal having intensity equivalent to that of the test signal in the reference region requires enormous labor and is difficult in practice. On the other hand, according to the present invention, since intensity of a signal generated depending on the amount of the metal compound to be applied exhibits stable reproducibility, it is easy to adjust the signal to desired intensity.

As an embodiment of the detection device of the present invention provided with a plurality of strips, there can be mentioned one having a structure in which a plurality of strips are radially arranged, and development can be performed for these strips at the same time by one injection operation of injecting a sample (developing liquid) from a sample injection hole disposed at the center. In the semi-quantifying measurement, according to this embodiment of the detection device of the present invention, the sample loading and developing operation can be performed as a single simultaneous loading and developing operation, which must be repeated as many times as the number of the strips when a plurality of detection devices each provided with one strip are used. As a result, operatability of the measurement is improved, and measurement errors that can occur in repetitive operations can be minimized.

The detection device of the present invention as described above can be prepared by radially arranging the strips on a substrate, placing a cover for fixing the strips and forming a sample injection hole at the center with a sample injection hole constituting member.

The substrate has a structure that enables radial (preferably, radial and symmetrical) arrangement of a plurality of strips depending on the number of the strips. FIG. 1 shows one example of the substrate. A substrate 1 shown in FIG. 1 is provided with such a recessed portion 2 that three strips can be placed radially and in three-fold symmetry. As a material of the substrate, usually a waterproof material is used, and for example, a synthetic resin, paper having waterproof property (or subjected to waterproof treatment) and so forth can be mentioned. In view of disposal of the device after use, a paper material is preferred.

The recessed portion 2 is used to place the strips, and consists of a circular portion at the center and rectangular portions radially extending therefrom. The recessed portion 2 usually has a depth of about 2 mm.

Figure 2:
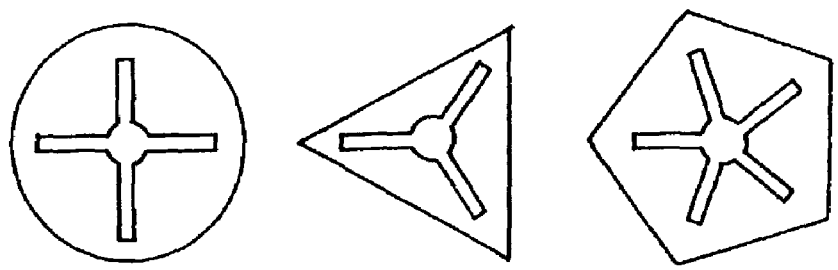
FIG. 2 shows exemplary shapes of the substrate and layout of recessed portions.
Figure 2:
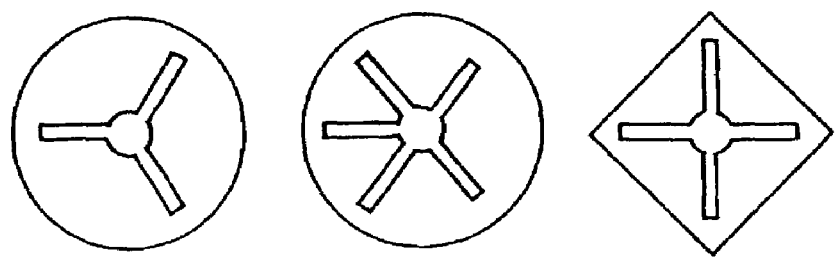
Figure 2:
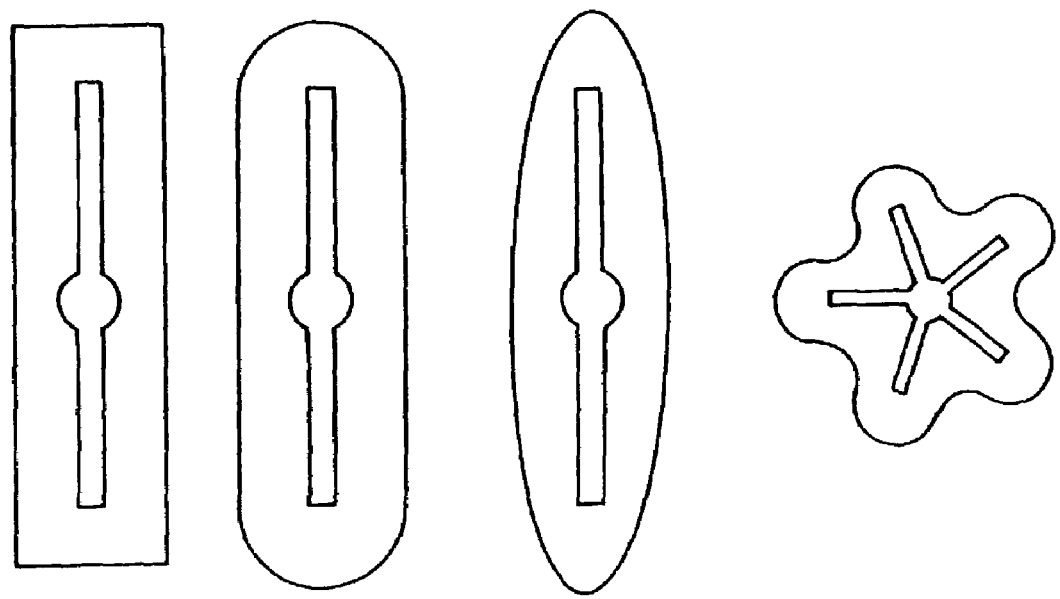

The shape of the substrate and layout of the recessed portion are not particularly limited. When two strips are used, it may be in a shape of rectangle of which ends may be circular or oblong. When three or more are used, in addition to a circular shape, a regular triangle, square, regular pentagon and other shapes can be used depending on the number of strips (FIG. 2).

The size of the substrate is selected depending on the size of a strip to be used. In the case of a circular shape, its radius is usually about 5–10 cm.

Figure 3:
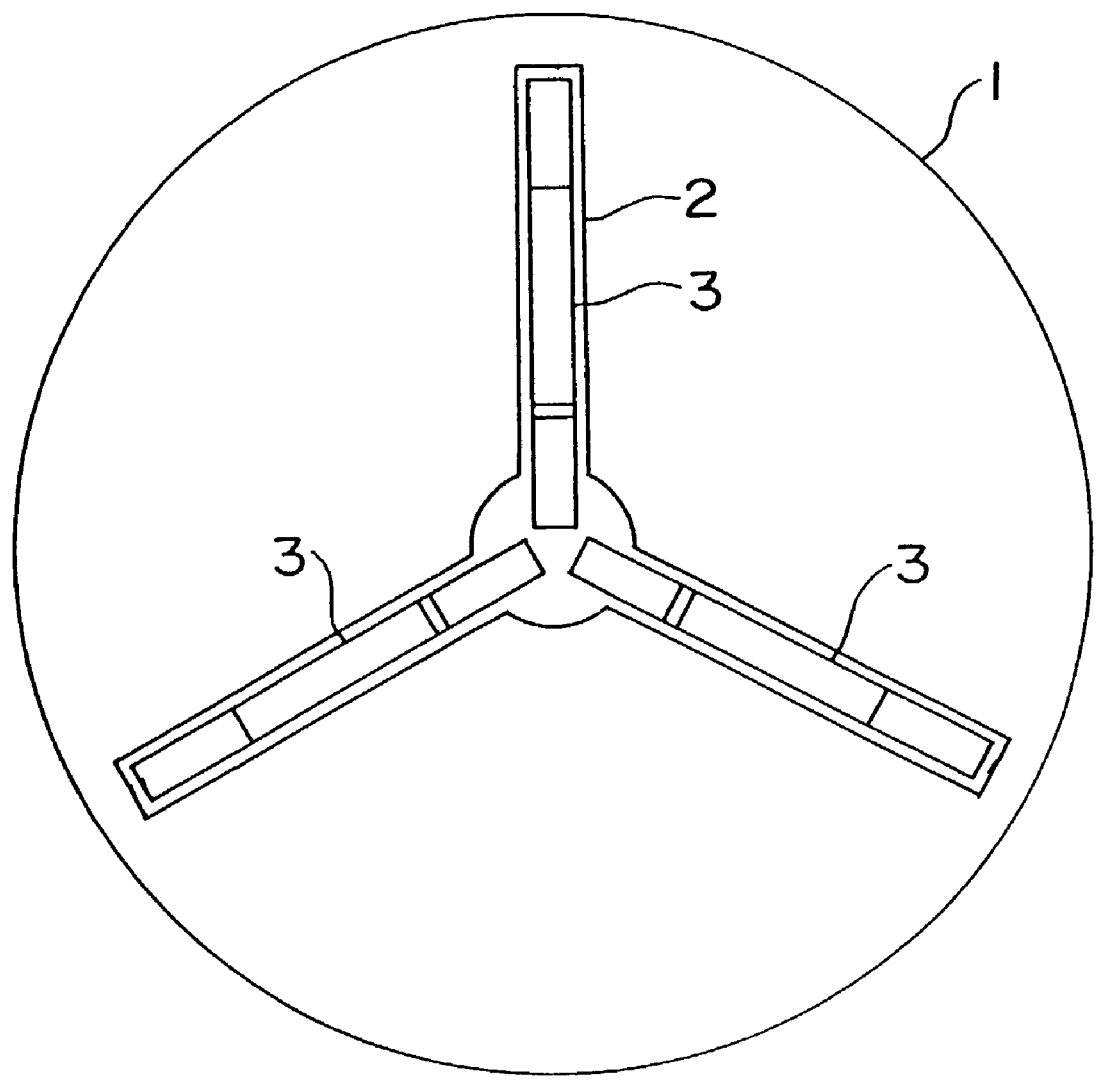
FIG. 3 shows the substrate shown in FIG. 1 on which strips are disposed.

As shown in FIG. 3, the strips 3 are arranged in the rectangular portions so that a part of one end thereof (on the upstream side in the developing direction) should be each protruded into the circular portion of the recessed portion at the center of the substrate. The circular portion at the center is a space for placing a pad for temporarily holding the sample (developing liquid). The size of the circular portion varies depending on volume of the pad required to hold a liquid amount necessary for development, but is usually about 1–2.5 cm in diameter. The dimension of the rectangular portion is selected depending on the size of the strip 3 to be used, but is usually about 5.5–8.5 mm in width.

The cover is bonded on the substrate to fix the strips, which are placed on the substrate, and may be in a plate-like or film-like shape. A material for the cover may be the same as that of the substrate.

Figure 4:
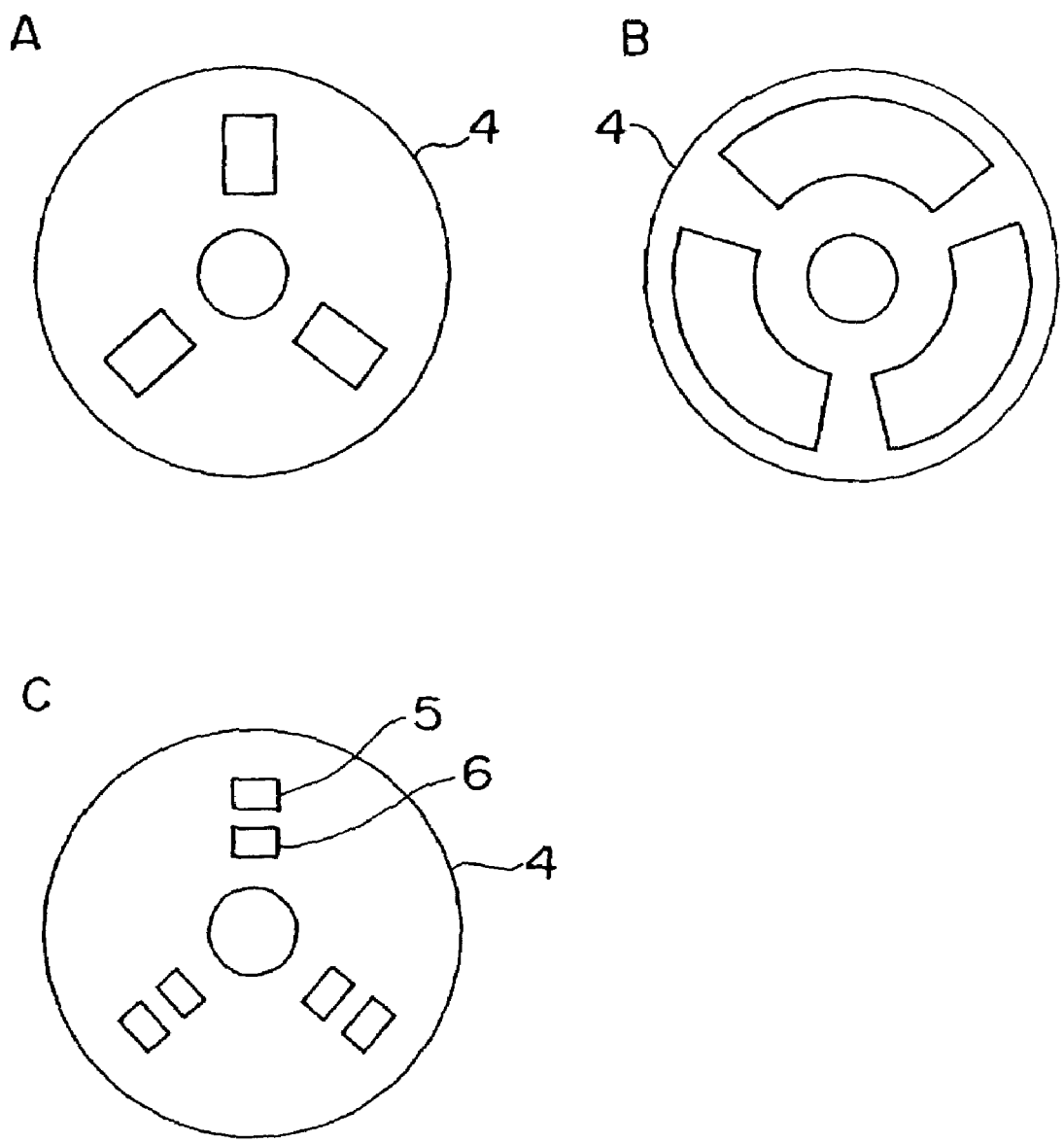
FIG. 4 shows exemplary layout of observation ports in a cover.

As shown in FIG. 4, a portion of the cover 4 corresponding to the recessed circular portion at the center of the substrate is cut out in the same shape. A portion for covering the strips is made transparent or cut out to form an observation port so that signals generated in the test region and the reference region can be observed.

The position, shape, size and so forth of the observation port are not particularly limited so long as both of the test signal and the reference signal can be observed and comparison can be readily performed. However, the upstream side end portions of the strips and absorbing pad portions attached at the furthest downstream (closest to the circumference) so as to efficiently progress development of the developing liquid are portions where a relatively large amount of a sample (serum, plasma, blood components, urine and so forth or a diluted solution thereof) is held, it is preferable to completely cover these portions so as not to be carelessly touched in view of prevention of a hazard. Examples of layout of the observation ports are shown in FIGS. 4, A–C. The observation port may be divided into two separate ports for the test region 6 and the reference region 5 as shown in FIG. 4, C.

A display indicating concentration of each strip (for example, numerals) is preferably provided on the cover.

Figure 5:
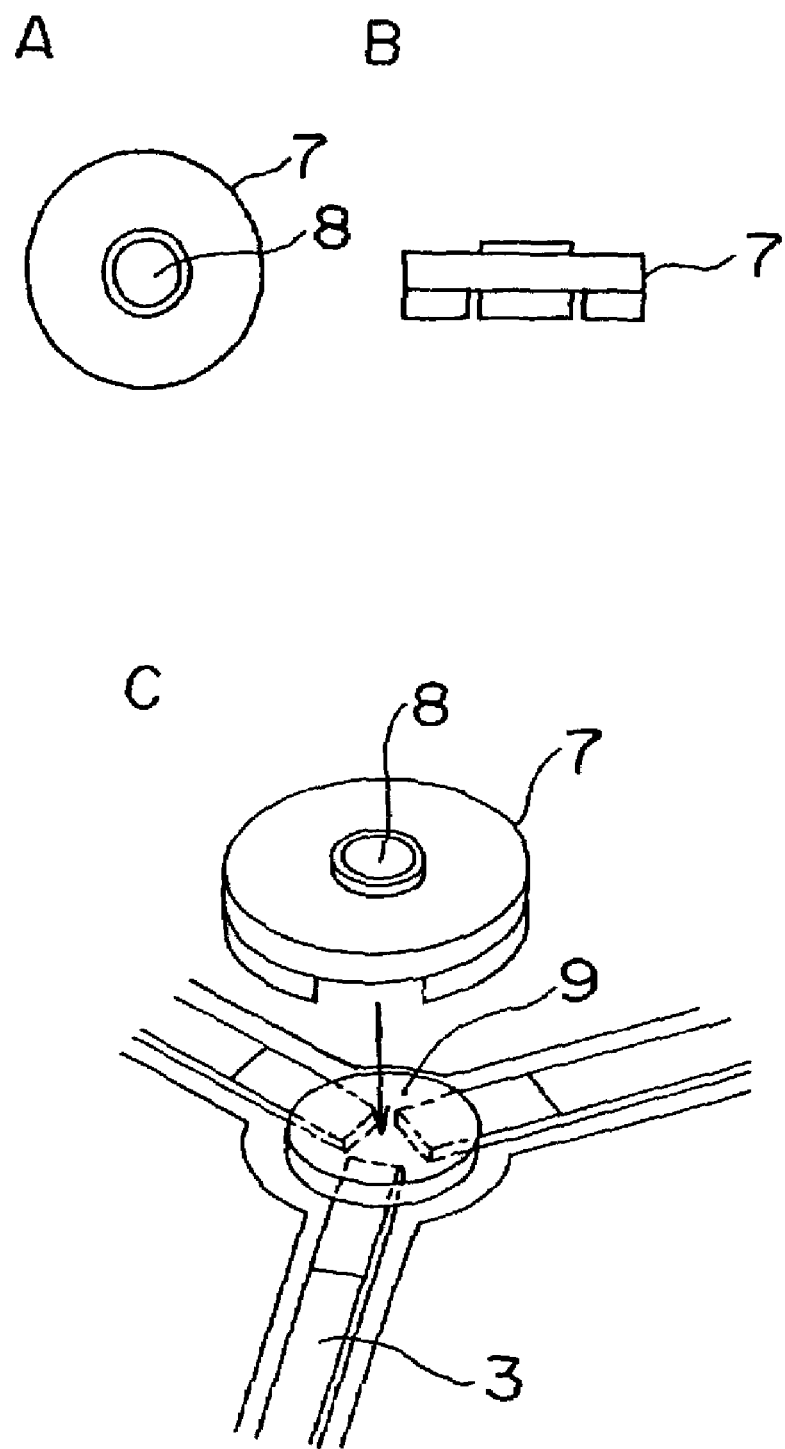
FIG. 5 shows an exemplary injection hole constituting member.

The sample injection hole is provided by a sample injection hole constituting member. The sample injection hole constituting member 7 has a shape having a recessed hole at its center, for example, as shown in FIG. 5, A and B. As the material, a synthetic resin and so forth can be mentioned. As shown in FIG. 5, C, a pad 9 is placed on the ends of the strips 3 at the center of the recessed circular portion, and a sample injection hole 8 is formed by engaging the sample injection hole constituting member 7 into the cut-out portion at the center of the cover (not shown) so as to press the pad 9. Since the pad 9 is placed immediately below this hole and further the pad 9 is in contact with the end portions of the radially arranged strips 3 on the upstream side, when a sample is injected from the sample injection hole 8, the injected sample is once absorbed and held in the pad 9 and gradually developed towards the downstream of each strip 3 (from the center radially to the circumferential directions).

The sample injection hole constituting member may be integrated with the cover. In this case, the pad is placed on the ends of strips in the circular portion of the substrate, and the cover is bonded to the substrate so as to press the pad.

In the above example, a recessed portion for placing the strips is provided in the substrate, but the recessed portion may be provided in the cover or in both of the substrate and the cover so long as the strips can be placed between the substrate and the cover when the substrate and the cover are bonded.

As a method for confirming a captured immune complex in the test region in immunochromatography, there are proposed a method of utilizing enzyme labeling and performing appropriate color developing treatment after development, a method of labeling with magnetic particles and mechanically measuring magnetic charge of the test region and so forth, instead of using the aforementioned colored particles. The present invention can also be applied as a method for confirming completion of development in a system using any of these methods for confirming test regions. That is, by preliminarily labeling a protein component or the like not involved in an antigen-antibody reaction in the test region of the test system at all with metal colloid, latex or the like, which consists of colored particles, allowing this protein to coexist in the developing liquid beforehand, and providing a reference region to which a metal compound is applied further downstream from the test region, the labeled substance can be captured and accumulated to generate a development completion signal.

The detection method of the present invention is a method for detecting a substance including development of a developing liquid through a test region up to a reference region, wherein the reference region contains a metal compound that is not an alkali metal salt and a label that can be accumulated in the reference region is contained in the developing liquid that reaches the reference region.

The detection method of the present invention is a kind of the solution development method. The detection method of the present invention may have the same configuration as that of a conventional detection method except that the reference region contains a metal compound that is not an alkali metal salt and a label that can be accumulated in the reference region is contained in the developing liquid that reaches the reference region.

The developing liquid, test region, reference region, alkali metal salt, label that can be accumulated in the reference region and developing liquid that reaches the reference region in the detection method of the present invention are similar to those described for the detection device of the present invention. Therefore, the detection method of the present invention can be implemented by using the detection device of the present invention.

Further, in the detection method of the present invention, a metal compound that is not an alkali metal salt is preferably contained in the reference region so that a signal having intensity equivalent to intensity of a signal generated in the test region when a developing liquid containing a predetermined amount of a substance to be detected is developed should be generated in the reference region, and the method preferably also includes comparison of intensities of a signal generated in the test region and a signal generated in the reference region. In this case, it is further preferred that a plurality of development carriers each having a test region and a reference region should be prepared so that intensity of a signal generated in each reference region should be equivalent to intensity of a signal generated in each corresponding test region when developing liquids containing the substance to be detected in different predetermined amounts are developed. In order to prepare a plurality of development carriers each having a test region and a reference region, the detection device of the present invention provided with a plurality of development carriers each having a test region and a reference region or a plurality of the detection devices of the present invention may be prepared.

EXAMPLES

The present invention will be explained more specifically with reference to the following test examples and examples. However, the scope of the present invention is not limited by these examples.

Test Example 1

This test was performed to investigate presence or absence of generation of a development completion signal by various kinds of metal compounds as well as effects of type and particle size of colored particles.

(1) Metal compound samples
Sample 1: Calcium acetate monohydrate (Kanto Kagaku)
Sample 2: Lanthanum acetate n-hydrate (Wako Pure Chemical Industries)
Sample 3: Lanthanum chloride heptahydrate (Kanto Kagaku)
Sample 4: Cerium acetate monohydrate (Wako Pure Chemical Industries)
Sample 5: Cerium(III) chloride heptahydrate (Kanto Kagaku)
Sample 6: Praseodymium acetate n-hydrate (Wako Pure Chemical Industries)
Sample 7: Neodymium acetate n-hydrate (Wako Pure Chemical Industries)

Sample 8: Erbium acetate tetrahydrate (Wako Pure Chemical Industries)
Sample 9: Manganese acetate tetrahydrate (Kanto Kagaku)
Sample 10: Iron(II) sulfate heptahydrate (Wako Pure Chemical Industries)
Sample 11: Ammonium iron(II) sulfate hexahydrate (Wako Pure Chemical Industries)
Sample 12: Cobalt(II) acetate tetrahydrate (Kanto Kagaku)
Sample 13: Nickel(II) acetate tetrahydrate (Kanto Kagaku)
Sample 14: Copper(II) acetate monohydrate (Kanto Kagaku)
Sample 15: Copper(II) chloride dihydrate (Kanto Kagaku)
Sample 16: Copper(II) sulfate pentahydrate (Kanto Kagaku)
Sample 17: Zinc(II) acetate dihydrate (Kanto Kagaku)
Sample 18: Cadmium(II) acetate dihydrate (Kanto Kagaku)
Sample 19: Aluminum acetate (water-soluble) (Nakarai Tesque)
Sample 20: Aluminum potassium sulfate dodecahydrate (Nakarai Tesque)
Sample 21: Lead(II) acetate trihydrate (Kanto Kagaku)
Sample 22: Sodium Bromide (Wako Pure Chemical Industries)
Sample 23: Potassium chloride (Wako Pure Chemical Industries)

(2) Preparation of Detection Device Sample (a) Application of Metal Compound to Nitrocellulose Membrane A nitrocellulose membrane (Millipore, SRHF, 200 mm×200 mm) was shaken in 5 mM phosphate buffer containing 0.01% sodium dodecylsulfate (pH 7.5) for 15 minutes and dried overnight at 35° C. This nitrocellulose membrane was cut into a 200 mm (breadth)×30 mm (length) piece, and an aqueous solution of each metal compound sample was applied at a position of 8 mm from one end of the longer side (hereafter, referred to as upper end) by using an applicator (IVEK). Each metal compound sample was weighted in an amount of 20 mg in a small vessel, dissolved in 1000 µl of distilled water, mixed with 50 µl of isopropyl alcohol by addition thereof and filtered through a 0.45-µm filter to obtain an aqueous solution for application. The solution for application was applied by using the applicator with a sweeping speed of 2.0 cm/sec, a discharge amount of the solution for application of 2.0 µl/sec, that is, an applied amount of the solution on the nitrocellulose membrane of 1 µl/cm (about 20 µg/cm in terms of a metal compound), and an application width of about 0.8 mm.

(b) Preparation of Labeled Antibody

Anti-human albumin monoclonal antibodies were labeled with gold colloid or latex with the following various particle sizes generally according to the method used in the Reference Examples 1 and 3 described later.

Gold colloid particle sizes: 8.5 nm, 15 nm, 25 nm and 40 nm

Latex particle sizes: 190 nm and 300 nm (c) Preparation of Developing Liquid

A mixture obtained by mixing the following solutions (i), (ii) and (iii) in proportions of 75:20:5 in volume was used as a developing liquid.
(i) 10 mM Tris, 150 mM NaCl (pH 7.6) (hereafter, abbreviated as 10 mM TBS (pH 7.6))
(ii) 10% Tween 20, 10 mM TBS (pH 7.6)
(iii) Each labeled anti-human albumin monoclonal antibody solution (3) Test Method A nitrocellulose membrane to which each of the metal compound samples was applied was cut into a piece with 5-mm width in the direction perpendicular to the application direction to obtain a test piece. 40 µl of the aforementioned developing liquid is placed on a microplate, brought into contact with the lower end of the test piece (end further from the applied position) and developed. When the developing liquid reached the upper end of the test piece, it was assumed that the development was completed, and there was determined the coloration caused by accumulation of the labeled antibodies at the position where the metal compound sample was applied. The coloration of each sample was determined by the following determination method with five test pieces for each metal compound sample.

(a) Method for Determining Coloration

Coloration of a reference region (position where a metal compound sample was applied) for confirming completion of development of each test piece was determined as follows.

The coloration was evaluated by visual observation and classified into four grades of no coloration (0 point), slight coloration (1 point), coloration (2 points) and strong coloration (3 points), and based on the mean values of the evaluation points, the coloration was determined as follows: a value lower than 0.5 point: no coloration, a value of 0.5 point or higher and lower than 1.5 points: slight coloration, a value of 1.5 points or higher and lower than 2.5 points: coloration, and a value of 2.5 points or higher and lower than 3.0 points: strong coloration.

(4) Test Results

The results of this test are shown in Table 1. As clearly seen from the results shown in Table 1, it was revealed that there was no coloration and generation of a development completion signal was not observed when the metal compound was an alkali metal salt such a sodium bromide and potassium chloride. Further, it was found that latex having a larger particle size than that of gold colloid showed an excellent coloration degree as the colored particles. Further, it was also found that gold colloid having a particle size of at least 15 nm showed an excellent coloration degree. Further, it was found that, since lanthanum acetate n-hydrate, lanthanum chloride heptahydrate, cerium acetate monohydrate, cerium(III) chloride heptahydrate, praseodymium acetate n-hydrate, neodymium acetate n-hydrate, erbium acetate tetrahydrate, iron(II) sulfate heptahydrate or iron(II) ammonium sulfate hexahydrate showed excellent coloration degree as a metal compound even when gold colloid having a relatively small particle size of 15 nm was used as colored particles, these metal compounds are preferred.

When each of the detection device samples was prepared with appropriate change of type of the nitrocellulose membrane, label or developing liquid and tested, almost the same results were obtained.

Further, when metal compounds except for alkali metal salts, potassium permanganate, anhydrous copper sulfate and anhydrous cobalt chloride were tested by using latex as the colored particles while appropriately changing the types of the metal compounds, there were obtained almost the same results that coloration was observed.

TABLE 1

| Sample No. | Gold colloid | | | | Latex | |
|---|---|---|---|---|---|---|
| | 8.5 nm | 15 nm | 25 nm | 40 nm | 190 nm | 300 nm |
| 1 | Coloration | Coloration | Strong coloration | Strong coloration | Strong coloration | Strong coloration |
| 2 | Coloration | Strong coloration | Strong coloration | Strong coloration | Strong coloration | Strong coloration |
| 3 | Coloration | Strong coloration | Strong coloration | Strong coloration | Strong coloration | Strong coloration |
| 4 | Coloration | Strong coloration | Strong coloration | Strong coloration | Strong coloration | Strong coloration |
| 5 | Coloration | Strong coloration | Strong coloration | Strong coloration | Strong coloration | Strong coloration |
| 6 | Coloration | Strong coloration | Strong coloration | Strong coloration | Strong coloration | Strong coloration |
| 7 | Coloration | Strong coloration | Strong coloration | Strong coloration | Strong coloration | Strong coloration |
| 8 | Coloration | Strong coloration | Strong coloration | Strong coloration | Strong coloration | Strong coloration |
| 9 | Slight coloration | Coloration | Coloration | Coloration | Strong coloration | Strong coloration |
| 10 | Coloration | Strong coloration | Strong coloration | Strong coloration | Strong coloration | Strong coloration |
| 11 | Coloration | Strong colaration | Strong coloration | Strong coloration | Strong coloration | Strong coloration |
| 12 | No coloration | No coloration | No coloration | No coloration | Coloration | Coloration |
| 13 | No coloration | No coloration | No coloration | No coloration | Coloration | Coloration |
| 14 | Slight coloration | Coloration | Coloration | Coloration | Strong coloration | Strong coloration |
| 15 | Slight coloration | Coloration | Coloration | Coloration | Strong coloration | Strong coloration |
| 16 | Slight coloration | Coloration | Coloration | Coloration | Strong coloration | Strong coloration |
| 17 | Slight coloration | Slight coloration | Slight coloration | Slight coloration | Coloration | Coloration |
| 18 | Slight coloration | Slight coloration | Slight coloration | Slight coloration | Coloration | Coloration |
| 19 | No coloration | No coloration | No coloration | No coloration | Strong coloration | Strong coloration |
| 20 | No coloration | No coloration | No coloration | No coloration | Strong coloration | Strong coloration |
| 21 | Coloration | Coloration | Strong coloration | Strong coloration | Strong coloration | Strong coloration |
| 22 | No coloration | No coloration | No coloration | No coloration | No coloration | No coloration |
| 23 | No coloration | No coloration | No coloration | No coloration | No coloration | No coloration |

Test Example 2

This test was performed to investigate the relationship between amount of a metal compound applied on the nitrocellulose membrane and coloration degree.

(1) Metal Compound Sample

Lanthanum acetate n-hydrate (Wako Pure Chemical Industries)

(2) Preparation of Detection Device Sample (a) Application of Metal Compound to Nitrocellulose Membrane The metal compound sample was applied to a nitrocellulose membrane by the application method described in the Test example 1, but the application amount was changed to 20, 5, 1.25, 0.63 and 0.16 μg/cm.

(b) Preparation of Labeled Antibody

Labeled antibodies were prepared by the preparation method described in Test example 1, but latex having a particle size of 190 nm was used.

(c) Preparation of developing liquid

A developing liquid was prepared by the preparation method described in the Test example 1.

(3) Test Method

The coloration of each sample was determined by using five test pieces for each kind of sample by the determination method described in Test example 1.

(4) Test Result

The results of this test are shown in Table 2. As seen from the results shown in Table 2, it was found that if the amount of the metal compound applied to the nitrocellulose membrane was at least 1.25 μg/cm, excellent coloration degree was obtained.

When each of the detection device samples was prepared with appropriate change of type of the nitrocellulose membrane, label or developing liquid and tested, almost the same results were obtained.

Further, when metal compounds except for alkali metal salts, potassium permanganate, anhydrous copper sulfate and anhydrous cobalt chloride were tested by using latex as the colored particles while appropriately changing the types of the metal compounds, there were obtained almost the same results.

TABLE 2

| Application amount of sample (μg/cm) | Coloration degree |
|---|---|
| 20 | Strong coloration |
| 5 | Strong coloration |
| 1.25 | Strong coloration |
| 0.63 | Coloration |
| 0.16 | Coloration |

Reference Example 1

Preparation of Latex Labeled Anti-human Albumin Monoclonal Antibody

To 34.5 μl of anti-human albumin monoclonal antibodies (Nihon Biotest Laboratories, 10 mg/ml), 0.1 ml of red polystyrene latex particles (JSR, 10 w/v %) having a particle size (particle diameter measured by electron microscopy) of 190 nm and 0.9 ml of a buffer were added, and the mixture was stirred whole day and night at room temperature, and then centrifuged (15000 rpm for 20 minutes) at 4° C. Then, the precipitation was suspended in a buffer containing 0.5% bovine serum albumin (Sigma) and 0.1% sodium azide (Nakarai Tesque) and dispersed by ultrasonication to obtain a suspension of monoclonal antibody-immobilized latex particles that specifically bound to human serum albumin.

Reference Example 2

Preparation of Rabbit Anti-human Lactoferrin Polyclonal Antibody

As an immunogen, a physiological saline solution (4 mg/ml) of human lactoferrin (Sigma, L-0520) was mixed with an equivalent amount of Freund's complete adjuvant (Difco), and emulsified into a water-in-oil type emulsion, and Japanese white rabbit (body weight: 3 kg, male) was immunized by intracutaneous injection of the emulsion (2 mg as human lactoferrin). Thereafter, while an antibody titer was monitored, the rabbit was given with booster every 4 weeks (0.5 mg as human lactoferrin per one booster). At the point when a rise of the antibody titer was confirmed, the booster was terminated, and blood was collected to obtain an antiserum. This antiserum was subjected to salting out with 50% saturated ammonium sulfate to obtain a crude IgG fraction. The obtained fraction was dissolved in 10 mM phosphate buffer (pH 8.0) and subjected to gel filtration by using a Sephadex G-25 column equilibrated with the same buffer beforehand to obtain an immunoglobulin fraction, which was then lyophilized and stored.

Reference Example 3

Preparation of Gold Colloid Labeled Anti-human Lactoferrin Monoclonal Antibody

In an amount of 1.0 ml mouse anti-human lactoferrin monoclonal antibody (Hytest, 4L2, clone: 2B8, phosphate buffer (pH 7.4)) was dialyzed overnight against 2 mM $Na_2B_4O_7$ buffer (pH 9.0) at 4° C.

20 ml of a solution of gold colloid having a particle size of 15 nm (British Biocell, EMGC15) was adjusted to pH 9.0 with addition of 0.2 M potassium carbonate aqueous solution and 264 μl of the antibody solution was added thereto. The mixture was left standing for 10 minutes. Subsequently, to the solution, 2 ml of 10% BSA was added. The mixture was left standing for 10 minutes and centrifuged (35000 rpm for 1 hour), and the supernatant was removed. To the sediment, 20 ml of 20 mM TBS (20 mM Tris, 150 mM NaCl, pH 8.0) containing 1% BSA was added. The mixture was centrifuged (35000 rpm for 1 hour) again, and the supernatant was removed. The precipitated gold colloid-labeled antibodies were suspended in 20 mM TBS containing 1% BSA and 0.05% sodium azide (Nakarai Tesque) to obtain a total volume of 1 ml and stored at 4° C.

Example 1

Preparation of Detection Device (Test Piece)

(1) Application of Anti-human Albumin Polyclonal Antibody to Test Region on Nitrocellulose Membrane Anti-human albumin polyclonal antibodies (Bethyl, 10 mM phosphate buffer, 150 mM NaCl) were diluted 25-fold with 10 mM phosphate buffer (pH 7.4). Isopropyl alcohol was added thereto in such an amount that the final concentration of isopropyl alcohol should become 5% v/v and the mixture was filtered through a 0.45-μm filter to obtain a solution for application.

A nitrocellulose membrane (Millipore, SRHF) was cut into a 200 mm (breadth)×30 mm (length) piece, and the aforementioned solution for application was applied thereto at a position of 12 mm from one end of the longer side (hereafter, referred to as lower end) by using an applicator (IVEK) with a sweeping speed of 2.0 cm/sec, a discharge amount of the solution for application of 2.0 μl/sec, that is, an applied amount of the solution on the nitrocellulose membrane of 1 μl/cm, and an application width of about 0.8 mm.

After the application, the membrane was dried at 35° C. for 2 hours, shaken in a 0.5% aqueous solution of polyvinylpyrrolidone K-15 for 15 minutes to perform blocking, then shaken in a 5 mM phosphate buffer (pH 7.5) containing 0.01% sodium dodecylsulfate for 15 minutes for washing and dried overnight at 35° C.

(2) Application of Lanthanum Acetate n-hydrate to Reference Region on Nitrocellulose Membrane.

Lanthanum acetate n-hydrate (Wako Pure Chemical Industries) was dissolved in distilled water to prepare an aqueous solution at a concentration of 0.2 mg/ml. Isopropyl alcohol was added thereto in such an amount that the final concentration of isopropyl alcohol should become 5% v/v, and the mixture was filtered through a 0.45-μm filter to obtain a solution for application.

The lanthanum acetate solution for application was applied on the nitrocellulose membrane prepared in the above (1) at a position of 8 mm from the upper end by using an applicator (IVEK) with a sweeping speed of 2.0 cm/sec, a discharge amount of the solution for application of 2.0 μl/sec, that is, an applied amount of lanthanum acetate on the nitrocellulose membrane of 1 μl/cm (about 0.2 μg/cm in terms of lanthanum acetate n-hydrate), and an application width of about 0.8 mm.

After the application, the membrane was dried overnight at 35° C. and stored at room temperature and humidity of 30–50%.

Subsequently, the membrane was cut into a piece with 5-mm width along the direction perpendicular to the application direction to obtain a detection device (test piece) for immunochromatography.

[Detection Method]

(1) Solution of Human Albumin as Substance to be Detected

In an amount of 5.0 mg of human albumin (Sigma) was weighted and dissolved in 10 mM Tris, 150 mM NaCl (pH 7.4) (hereafter, abbreviated as 10 mM TBS (pH 7.4)) to obtain a total volume of 1.0 ml. This solution was used as a stock solution and successively diluted with 10 mM TBS (pH 7.4) to prepare solutions at the following concentrations.

(a) 20 µg/ml, (b) 5.0 g/ml, (c) 1.2 µg/ml, (d) 0.3 µg/ml, (e) 0.08 µg/ml and (f) 0 µg/ml (2) Labeled Antibody As labeled anti-human albumin monoclonal antibodies, latex-labeled anti-human albumin monoclonal antibodies prepared according to the method descried in Reference Example 1 were used.

(3) Developing Liquid

A mixture obtained by mixing the following solutions (i), (ii), (iii) and (iv) in proportions of 65:20:10:5 in volume was used as a developing liquid.

(i) 10 mM TBS (pH 7.6)
(ii) 10% Tween 20, 10 mM TBS (pH 7.6)
(iii) Human albumin solution at each concentration
(iv) Labeled anti-human albumin monoclonal antibody solution Therefore, the final concentration of human albumin, which was a substance to be detected, in each developing liquid was 1/10 of the concentration of each human albumin solution described in the aforementioned (1).

(4) Detection Operation

In an amount of 40 µl of the developing liquid was placed on a microplate, brought into contact with the lower end of the detection device (test piece) and developed. When the developing liquid reached the upper end of the test piece, it was assumed that the development was completed, and the coloration caused by accumulation of the labeled antibodies in the test region to which the anti-human albumin polyclonal antibodies were applied and the reference region to which the lanthanum acetate aqueous solution was applied was evaluated.

[Detection Results]

(1) Coloration in Test Region

Coloration dependent on the concentration of human albumin, which was the substance to be detected, was observed.

(2) Coloration in Reference Region

For all of the tested human albumin concentrations, the flow of the antibodies labeled with latex was blocked at a site to which lanthanum acetate was applied (reference region), generation of a band due to accumulation of the labeled antibodies could be visually observed, and thus a development completion signal was generated. It was found that the signal intensity of this reference region was attenuated as the concentration of human albumin, which was the substance to be detected, increased, that is, attenuated in reverse to the increase in the color intensity in the test region, but did not affect confirmation of completion of development.

Example 2

Preparation of Detection Device (Test Piece)

(1) Application of Anti-human Lactoferrin Polyclonal Antibody to Test Region on Nitrocellulose Membrane To a rabbit anti-human lactoferrin polyclonal antibody solution prepared according to the method described in Reference Example 2, isopropyl alcohol was added in such an amount that the final concentration of isopropyl alcohol should become 5% v/v, and the mixture was filtered through a 0.45-µm filter to obtain a solution for application.

A nitrocellulose membrane (Millipore, SRHF) was cut into a 200 mm (breadth)×30 mm (length) piece, and the aforementioned solution for application was applied at a position of 12 mm from one end of the longer side (hereafter, referred to as lower end) by using an applicator (IVEK) with a sweeping speed of 2.0 cm/sec, a discharge amount of the solution for application of 2.0 µl/sec, that is, an applied amount of the solution on the nitrocellulose membrane of 1 µl/cm, and an application width of about 0.8 mm.

After the application, the membrane was dried at 35° C. for 2 hours, shaken in a 0.5% aqueous solution of polyvinylpyrrolidone K-15 for 15 minutes to perform blocking, then shaken in a 5 mM phosphate buffer (pH 7.5) containing 0.01% sodium dodecylsulfate for 15 minutes for washing and dried overnight at 35° C.

(2) Application of cerium(III) Chloride Heptahydrate to Reference Region on Nitrocellulose Membrane Cerium(III) chloride heptahydrate (Kanto Kagaku) was dissolved in distilled water to prepare an aqueous solution at a concentration of 0.2 mg/ml. Isopropyl alcohol was added thereto in such an amount that the final concentration of isopropyl alcohol should become 5% v/v, and the mixture was filtered through a 0.45-µm filter to obtain a solution for application.

The cerium chloride solution for application was applied on the nitrocellulose membrane prepared in the above (1) at a position of 8 mm from the upper end by using an applicator (IVEK) with a sweeping speed of 2.0 cm/sec, a discharge amount of the solution for application of 2.0 µl/sec, that is, an applied amount of cerium chloride on the nitrocellulose membrane of 1 µl/cm (about 0.2 µg/cm in terms of cerium (III) chloride heptahydrate), and an application width of about 0.8 mm.

After the application, the membrane was dried overnight at 35° C. and stored at room temperature and humidity of 30–50%.

Subsequently, the membrane was cut into a piece with 5-mm width in the direction perpendicular to the application direction to obtain a detection device (test piece) for immunochromatography.

[Detection Method]

(1) Solution of Human Lactoferrin as Substance to be Detected 4.5 mg of human lactoferrin (Sigma: L0520) was weighted and dissolved (4 mg/ml) in 1125 µl of 10 mM TBS (pH 7.4). To 50 µl of the solution, 950 µl of 10 mM Tris, 150 mM NaCl (pH 8.0, hereafter, abbreviated as 10 mM TBS (pH 8.0)) was added to obtain a stock solution (200 µg/mL), and the stock solution was successively diluted with 10 mM TBS (pH 8.0) to prepare solutions having the following concentrations.

(a) 128 µg/ml, (b) 32 µg/ml, (c) 8.0 µg/ml, (d) 2.0 µg/ml, (e) 0.5 µg/ml and (f) 0 µg/ml (2) Labeled Antibody As labeled anti-human lactoferrin monoclonal antibodies, gold colloid labeled anti-human lactoferrin monoclonal antibodies prepared according to the method descried in Reference Example 3 were used.

(3) Developing Liquid

A mixture obtained by mixing the following solutions (i), (ii), (iii) and (iv) in proportions of 65:20:10:5 in volume was used as a developing liquid.
(i) 10 mM TBS (pH 8.0)
(ii) 10% Tween 20, 10 mM TBS (pH 8.0)
(iii) Human lactoferrin solution at each concentration
(iv) Labeled anti-human lactoferrin monoclonal antibody solution Therefore, the final concentration of human lactoferrin which was a substance to be detected, in each developing liquid was 1/10 of the concentration of each lactoferrin solution described in the aforementioned (1).

(4) Detection Operation

In an amount of 40 µl of the developing liquid was placed on a microplate, brought into contact with the lower end of the detection device (test piece) and developed. When the developing liquid reached the upper end of the test piece, it was assumed that the development was completed, and coloration caused by accumulation of the labeled antibodies in the test region to which the anti-human lactoferrin polyclonal antibodies were applied and the reference region to which the cerium chloride aqueous solution was applied was evaluated.

[Detection Results]

(1) Coloration in Test Region

Coloration dependent on the concentration of human lactoferrin, which was the substance to be detected, was observed.

(2) Coloration in Reference Region

For all of the tested human lactoferrin concentrations, the flow of the antibodies labeled with gold colloid was blocked at a site to which the cerium chloride aqueous solution was applied (reference region), generation of a band due to accumulation of the labeled antibodies could be visually observed, and thus a development completion signal was generated. It was found that the signal intensity of this reference region was attenuated as the concentration of human lactoferrin, which was a substance to be detected, increased, that is, in reverse to the increase in the color intensity in the test region, but did not affect confirmation of completion of development.

Example 3

Preparation of Detection Device (Test Piece)

(1) Application of Anti-human Albumin Monoclonal Antibody to Test Region on Nitrocellulose Membrane 90 µl of anti-human albumin monoclonal antibody solution (Nihon Biotest Laboratories, #303, 10 µg/µl in 10 mM phosphate buffer, 150 mM NaCl, pH 7.2) was mixed with 765 µl of 10 mM phosphate buffer (pH 7.2) and 45 µl of isopropyl alcohol (hereafter, referred to as IPA) by addition thereof for 10-fold dilution to obtain a solution for application (antibody concentration: 1.0 µg/l).

A nitrocellulose membrane (Millipore, SNHF) was cut into a 200 mm (breadth)×25 mm (length) piece, and the aforementioned solution for application was applied at a position of 8 mm from one end of the longer side (hereafter, referred to as lower end) by using an applicator (IVEK) with a sweeping speed of 5.0 cm/sec, a discharge amount of the solution for application of 2.0 µl/sec, that is, an applied amount of the solution on the nitrocellulose membrane of 0.4 µl/cm, and an application width of about 0.4 mm.

After the application, the membrane was dried at 35° C. for 2 hours, shaken in a 0.5% aqueous solution of polyvinylpyrrolidone K-15 for 15 minutes to perform blocking, shaken in a 5 mM phosphate buffer (pH 7.5) containing 0.01% sodium dodecylsulfate for 15 minutes for washing and dried overnight at 35° C.

(2) Application of Lanthanum Acetate to Reference Region on Nitrocellulose Membrane In an amount of 30.0 mg of lanthanum acetate n-hydrate (Wako Pure Chemical Industries) was weighted and completely dissolved in 1500 µl of distilled water and filtered through a 0.45-µm filter to obtain a stock solution. 200 µl of the stock solution was mixed with 750 µl of distilled water and 50 µl of IPA by addition thereof to prepare Solution for application A (lanthanum acetate concentration: 4.0 µg/µl). Subsequently, 175 µl of the stock solution was mixed with 775 µl of distilled water and 50 µl of IPA by addition thereof to prepare Solution for application B (lanthanum acetate concentration: 3.5 µg/µl). Further, 150 µl of the stock solution was mixed with 800 µl of distilled water and 50 µl of IPA by addition thereof to prepare Solution for application C (lanthanum acetate concentration: 3.0 µg/µl). Then, by a similar procedure, Solution for application D (lanthanum acetate concentration: 2.5 µg/µl), Solution for application E (lanthanum acetate concentration: 2.0 µg/µl), Solution for application F (lanthanum acetate concentration: 1.5 µg/µl), Solution for application G (lanthanum acetate concentration: 1.0 µg/µl), Solution for application H (lanthanum acetate concentration: 0.5 µg/µl), Solution for application I (lanthanum acetate concentration: 0.24 µg/µl) and Solution for application J (acetate lanthanum concentration: 0.12 µg/µl), wherein the final concentration of IPA was 5% v/v, were prepared by changing the amounts of the stock solution and the distilled water.

The lanthanum acetate solutions containing 5% IPA (Solutions for application A-J) were each applied on the nitrocellulose membrane to which the anti-human albumin monoclonal antibodies were applied, which was prepared in the above (1), at a position of 8 mm from the upper end by using an applicator (IVEK) with a sweeping speed of 5.0 cm/sec, a discharge amount of the solution for application of 2.0 µl/sec, that is, an applied amount of the solution on the nitrocellulose membrane of 0.4 µl/cm and an application width of about 0.4 mm. After the application, the membranes were dried overnight at 35° C. and stored at room temperature and humidity of 30–50%.

Subsequently, the membranes were each cut into a piece with 5-mm width in the direction perpendicular to the application direction to obtain detection devices (test pieces) for immunochromatography. That is, prepared were test pieces having applied amounts of lanthanum acetate applied to the reference region on the nitrocellulose membrane of 1.6 µg/cm (Test piece A), 1.4 µg/cm (Test piece B), 1.2 µg/cm (Test piece C), 1.0 µg/cm (Test piece D), 0.8 µg/cm (Test piece E), 0.6 µg/cm (Test piece F), 0.4 µg/cm (Test piece G), 0.2 µg/cm (Test piece H), 0.1 µg/cm (Test piece I) and 0.05 µg/cm (Test piece J), respectively.

[Detection Method]

(1) Preparation of Solution of Human Albumin as Substance to be Detected

In an amount of 5.0 mg of human albumin (Sigma) was weighted and dissolved in 10 mM Tris, 150 mM NaCl (pH 7.6) (hereafter, abbreviated as 10 mM TBS (pH 7.6)) to obtain a total volume of 1.0 ml. This solution was used as a stock solution and successively diluted with 10 mM TBS (pH 7.6) to prepare solutions having the following concentrations.

(a) 30 µg/ml, (b) 25 µg/ml, (c) 20 µg/ml, (d) 15 µg/ml, (e) 10 µg/ml, (f) 7.5 µg/ml, (g) 5.0 µg/ml, (h) 2.5 µg/ml, (i) 2.0 µg/ml, (j) 1.0 µg/ml, (k) 0.50 µg/ml and (l) 0 µg/ml (2) Labeled Antibody A labeled antibody solution was obtained by using anti-human albumin monoclonal antibodies (Nihon Biotest Laboratories, #301) and red polystyrene latex particles having a particle size of 190 nm (JSR) by the same method as described in Reference Example 1.

(3) Developing Liquid

A mixture obtained by mixing the following solutions (i), (ii), (iii) and (iv) in proportions of 65:20:10:5 in volume was used as a developing liquid.

(i) 10 mM TBS (pH 7.6)
(ii) 5% Tween 80, 10 mM TBS (pH 7.6)
(iii) Human albumin solution at each concentration prepared in the above (1)
(iv) Labeled anti-human albumin monoclonal antibody solution prepared in the above (2)

Therefore, the final concentration of human albumin which was a substance to be detected, in each developing liquid was 1/10 of the concentration of each human albumin solution described in the above (1).

(4) Detection Operation

In an amount of 40 µl of the developing liquid was placed on a microplate, brought into contact with the lower end of the detection device (test piece) and developed. When the developing liquid reached the upper end of the test piece, it was assumed that the development was completed, and intensities of a color development signal generated in the test region to which the anti-human albumin polyclonal antibodies were applied and a color development signal generated in the reference region to which the lanthanum acetate aqueous solution was applied were compared.

[Results]

In Test pieces A–J having different concentrations of lanthanum acetate applied to the reference region, which were prepared in the above (2), solutions having various concentrations of human albumin were developed. The results were as follows.

1. When a solution containing human albumin at a concentration of 2.0 µg/ml was developed through Test piece C, the test signal and the reference signal had almost equal intensities.
2. When a solution containing human albumin at a concentration of 1.0 µg/ml was developed through Test piece D, the test signal and the reference signal had almost equal intensities.
3. When a solution containing human albumin at a concentration of 0.5 µg/ml was developed through Test piece E, the test signal and the reference signal had almost equal intensities.
4. When a solution containing human albumin at a concentration of 0.1 µg/ml was developed through Test piece I, the test signal and the reference signal had almost equal intensities.

Further, the detection limit of human albumin in this immunochemical measurement system was determined to be around 0.05 µg/ml. On the other hand, with a developing liquid containing human albumin at a concentration of 3.0 µg/ml or higher, a so-called prozone phenomenon appeared, and a clear decrease of the test signal intensity was observed in comparison with the developing liquid containing human albumin at a concentration of 2.0 µg/ml.

Based on the above, it is recognized that the optimum detection range of this human albumin detection system is 0.05–2.0 µg/ml. The semi-quantification ability of these strips was further verified.

That is, based on the aforementioned results, semi-quantitative measurement of human albumin concentration in specimens was examined by using three kinds of strips of Test piece I, Test piece E and Test piece D.

Solutions having a known concentration of human albumin, wherein the final concentration of human albumin was 0.05–1.5 µg/ml, were newly prepared, developed through the aforementioned three kinds of strips at the same time. By visually comparing intensities of the test signals and the reference signals on the strips, the human albumin concentrations of the respective solutions were classified into 7 grades, (i) lower than about 0.1 µg/ml, (ii) about 0.1 µg/ml, (iii) between about 0.1 µg/ml and about 0.5 µg/ml, (iv) about 0.5 µg/ml, (v) between about 0.5 µg/ml and about 1.0 µg/ml, (vi) about 1.0 µg/ml and (vii) higher than about 1.0 µg/ml to examine the determination accuracy. As a result, it was confirmed that all of the solutions could be graded with favorable reproducibility in three trials.

INDUSTRIAL APPLICABILITY

There are provided a device for detecting a substance and method for detecting a substance suitable for detection of a substance using the solution development method. As described in detail above, major advantages provided by the present invention are as follows.

1) The device for detecting a substance according to the present invention is readily prepared and manufactured at a low cost, and a development completion signal and/or a reference signal do not fluctuate among preparation lots.
2) When the device for detecting a substance according to the present invention is used, a development completion signal and/or a reference signal are hardly discolored and hence storability of data is favorable.
3) According to the method for detecting a substance of the present invention, by using the reference region for confirming completion of development, the development completion signal can be reliably confirmed.
4) According to the method for detecting a substance of the present invention, by using the reference region to for generating a reference signal, semi-quantitative measurement can be conveniently and readily performed.

What is claimed is:

1. A method of detecting the presence of an analyte in a biological sample, comprising:
   (a) providing a development carrier comprising:
      (i) a test region to which a reactive substance 1 reactive with the analyte is bound; and
      (ii) a reference region to which a metal compound is bound, wherein the reference region contains a metal compound other than a compound selected from the group consisting of an alkali metal salt, anhydrous copper sulfate and anhydrous cobalt chloride;

(b) adding a labeled second reactive substance 2 reactive with the analyte to the biological sample;

(c) applying the biological sample from (b) to the development carrier;

(d) developing the biological sample through the test region and subsequently through the reference region, such that the labeled reactive substance 1 that has reacted with the analyte becomes bound to the test region and the labeled first substance that has not reacted with the analyte becomes non-specifically blocked by the metal compound; and (e) detecting the presence of the analyte by identifying the presence of the label at both the test region and the reference region.

2. A method for providing a reference signal when detecting a substance with a detection device, comprising:

developing a developing liquid comprising a labeled reactive substance 2 through a test region comprising a reactive substance 1 which is immobilized in the test region and capable of binding to reactive substance 2, and continuing to develop the developing liquid at least until the developing liquid contacts a reference region which comprises a metal compound other than a compound selected from the group consisting of an alkali metal salt, anhydrous copper sulfate and anhydrous cobalt chloride, wherein the labeled reactive substance 2 not bound to reactive substance 1 in the test region accumulates in the reference region thereby providing a reference signal.

3. The method according to claim 2, wherein the label is a colored particle.

4. The method according to claim 3, wherein the label is bound to reactive substance 2 and the reference signal is produced by accumulation of labeled reactive substance 2 not bound to reactive substance 1 in the reference region.

5. The method for detecting a substance according to claim 4, wherein the reactive substance 2 is an antibody or an antigen which binds to the substance to be detected.

6. The method according to claim 2, wherein the detection device comprises a nitrocellulose membrane.

7. The method according to claim 2, wherein the reference has an intensity equivalent to intensity of a signal generated in the test region when a predetermined amount of the substance to be detected is present in the developing liquid, and the method further comprises comparing the intensity of the signal generated in the test region with the intensity of the signal generated in the reference region, wherein when a greater signal is detected in the test region than in the reference region, the developing liquid has a lesser amount of the substance than the predetermined amount, and wherein when a lesser signal is detected in the test region than in the reference region, the developing liquid has a greater amount of the substance than the predetermined amount.

8. The method according to claim 7, wherein a plurality of development carriers each having a test region and a reference region are prepared, and the predetermined amounts are different for each of the carriers.

9. The method of claim 2, wherein the reference signal confirms completion of development.

10. The method of claim 2, wherein the reference signal is used to evaluate the test region.

11. A device comprising:

a development carrier comprising:

a test region comprising an immobilized reactive substance; and a reference region downstream from the test region, the reference region containing a metal compound other than a compound selected from the group consisting of an alkali metal salt, anhydrous copper sulfate and anhydrous cobalt chloride.

12. The detection device according to claim 11, wherein the development carrier is a nitrocellulose membrane.

13. The detection device according to claim 11, wherein the reference region comprises a predetermined amount of the metal compound so that a signal having an intensity equivalent to an intensity of a signal generated in the test region is generated when a developing liquid containing a predetermined amount of a substance to be detected comprising a label is added whereby the signal is provided by accumulation of the excess label not bound in the test region.

14. The detection device according to claim 13, wherein the detection device comprises a plurality of development carriers each having a test region and a reference region, and intensity of a signal generated in each reference region is equivalent to that of a signal generated in each corresponding test region when developing liquids containing the substance to be detected in different predetermined amounts comprising labels are developed, whereby signals are provided by accumulation of the labels and are different for each of the carriers.

* * * * *

UNITED STATES PATENT AND TRADEMARK OFFICE
CERTIFICATE OF CORRECTION

PATENT NO. : 7,090,984 B2 Page 1 of 1
APPLICATION NO. : 10/182477
DATED : August 15, 2006
INVENTOR(S) : Hashimoto et al.

It is certified that error appears in the above-identified patent and that said Letters Patent is hereby corrected as shown below:

Page 1, (73) Assignee, "Tokyo (JP)" should be changed to --Minato-ku, Tokyo, (JP)--

Column 15, Table 1, Line 11, $2^{nd}$ Column, "Strong colaration" should be changed to --Strong coloration--

Column 19, Line 15, "5.0 g/ml," should be changed to --5.0 µg/ml,--

Column 21, Line 65, "1.0 µg/l." should be changed to --1.0 µg/µl.--

Column 24, Line 2, "0.1 g/ml" should be changed to --0.1 µg/ml--

Signed and Sealed this

Twentieth Day of February, 2007

JON W. DUDAS
*Director of the United States Patent and Trademark Office*